Figure 1:
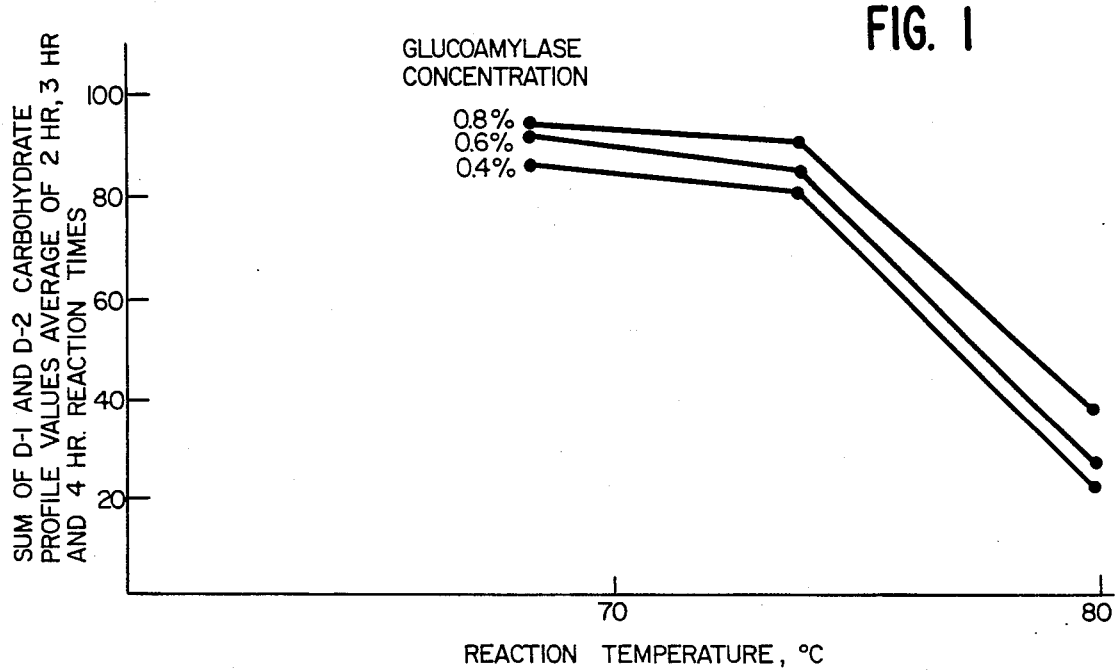

United States Patent [19]

Harvey et al.

[11] Patent Number: 4,622,299

[45] Date of Patent: Nov. 11, 1986

[54] PRODUCTION OF HIGH D.E. SYRUPS

[75] Inventors: Richard D. Harvey; Paul R. Witt, both of Muscatine, Iowa

[73] Assignee: Grain Processing Corporation, Muscatine, Iowa

[21] Appl. No.: 672,294

[22] Filed: Nov. 16, 1984

[51] Int. Cl.4 .................. C12P 19/20; C12R 1/66; C12R 1/845

[52] U.S. Cl. .................. 435/96; 435/913; 435/939

[58] Field of Search .......................... 435/96

[56] References Cited

U.S. PATENT DOCUMENTS

| | | | |
|---|---|---|---|
| 2,970,086 | 1/1961 | Kerr | 195/66 |
| 3,017,330 | 1/1962 | Kerr | 195/11 |
| 3,039,936 | 6/1962 | Lenney et al. | 195/11 |
| 3,280,006 | 10/1966 | Hurst et al. | 195/31 |
| 3,291,702 | 12/1966 | Miescher | 195/31 |
| 3,535,123 | 10/1970 | Heady | 99/142 |
| 3,630,845 | 12/1971 | Dworschack et al. | 195/31 |
| 3,806,415 | 4/1974 | Hayes | 195/31 |
| 3,897,305 | 7/1975 | Hurst | 195/31 |
| 3,922,197 | 11/1975 | Leach et al. | 195/31 |
| 3,922,198 | 11/1975 | Kusk et al. | 195/31 |
| 4,410,368 | 10/1983 | Takasaki et al. | 127/38 |
| 4,415,656 | 11/1983 | Rohrbach et al. | 435/96 |
| 4,536,477 | 8/1985 | Katkocin et al. | 435/205 |

OTHER PUBLICATIONS

Basic Biochemistry, 3rd edition, 1971, p. 56.
Fogarty et al, European J. Appl. Microbial Biotechnol. (1983) 18: 271-278.
Hakulin et al, Die Starke, 35 (1983) No. 12, s. 411-414.
Novo Enzymes Product Data Sheet, "AMG", Mar. 1980, 2 pages.

*Primary Examiner*—Lionel M. Shapiro
*Attorney, Agent, or Firm*—Neuman, Williams, Anderson & Olson

[57] ABSTRACT

A process for the conversion of starch to syrups having a dextrose equivalent (D.E.) value of at least 90 and is achieved by treating liquid starch with glucoamylase for a period of not more than three hours.

4 Claims, 2 Drawing Figures

PRODUCTION OF HIGH D.E. SYRUPS

This invention relates to the conversion of starch to high D.E. syrups. More particularly, the invention relates to a new and improved process for hydrolyzing starch to produce syrups containing high amounts of dextrose.

The production of syrups containing high levels of dextrose by enzymatic conversion of starch sources has been practiced for many years. In general, these known processes involve liquefying an aqueous suspension of starch by various means, such as by use of acids or enzymes or a combination of acid-enzyme or enzyme-enzyme. After liquefaction, the starch is saccharified at elevated temperatures up to about 60° C., with glucoamylase or amyloglucosidase to produce a syrup having a high content of dextrose. Typically, the saccharification times required in these processes for conversion of starch to high dextrose syrups range from at least 24 to 96 hours or more. See, for example, U.S. Pat. No. 2,970,086. Such processes, because of the long conversion times, require large reaction vessels and a large volume of substrate in order to be economically feasible. Such long conversion times are not conducive to continuous operation and the large substrate volumes present great potential for losses and involve processing difficulties attending the use of large volumes. The starch industry is continually seeking dextrose production procedures whereby starch can be converted to high D.E. syrups in shorter times. By reducing the time required for starch conversion, the volume of substrate being processed at a given time can be reduced significantly and a significant increase in production capacity can be realized.

It is therefore a principal object of the present invention to provide an improved process for the conversion of starch to dextrose.

It is another object of the present invention to provide a process in which starch is converted to dextrose in a short period.

It is another object of the invention to provide a process for treating starch to obtain a syrup having a dextrose equivalent value (D.E.) of at least 90 in a period of not more than three hours.

It is still another object of the invention to provide a process wherein starch is converted in a short period of time to provide a syrup containing a high level of dextrose which can be readily refined so as to be suitable for use in a wide variety of applications, such as analytical, food, pharmaceutical and medical use applications.

It is a still another object of the invention to provide a process wherein starch is converted in a short period of time which without further treatment or refinement is very suitable for use in alcohol production, fermentation and brewery applications.

In accordance with the new improved process of this invention, starch in aqueous suspension is liquefied, that is, the starch granules are pasted and the starch hydrated and dispersed to such an extent that hydrolytic cleavage of the starch molecules can be readily accomplished. Liquefaction can be accomplished using a variety of known procedures involving the use of acids such as hydrochloric, sulfuric or oxalic, or by use of enzymes such as bacterial alpha-amylase. The liquefaction is achieved by using acid, enzyme or combinations thereof at a relatively high temperature, such as above 90° C. Liquefaction is carried out for a period to insure that substantially all of the starch granules have become gelatinized as determined by the absence of birefringence. The D.E. value of the liquefied starch typically ranges from about 5 to 30. There are interdependent relationships between temperature, pH, time and type of treating agent employed with respect to accomplishing substantially complete liquefaction with controlled dextrinization and each is susceptible to variation within limits, as well known in the art.

It is preferred and advantageous to cook the starch prior to liquefaction. A particularly preferred procedure is to subject the starch slurry to heat in a jet cooker, which is a device currently used in the starch industry for cooking starches. In such cookers steam is directed into the flow path of the starch slurry. The steam and the slurry are intimately mixed and dynamically worked and then forced through one or more jet nozzle orifices. Generally, exposure of the starch slurry to heat in a jet cooker is conducted for short periods of from about 1 to 10 minutes and preferably from about 3 to 5 minutes. The starch is generally heated to temperatures on the order of 250° to 325° F. (121°–163° C.) in the jet cooker.

The starch may be any of those commonly available, including corn starch, waxy maize starch, tapioca starch, potato starch, white sweet potato starch, wheat starch, sago starch, sorghum starch, high amylose starch and the like. Waxy and the non-waxy starches are suitable. Corn grits and other raw materials high in starch content such as, for example, low D.E. starch hydrolyzates, may be used satisfactorily.

After liquefaction, the pH of the liquefied starch is adjusted to a pH of 4.0–4.7 and the gelatinized starch is saccharified with glucoamylase in a temperature range of 150° F. to 175° F. (65.5°–79.9° C.), preferably at a temperature of 160° F. to 165° F. (71°–73.9° C.), for a period of not more than 3 hours. The glucoamylase is used in critical amounts in the range of about 0.005 to 0.02 gram per gram of starch, dry basis. The glucoamylase employed can be any fungal glucoamylase such as those belonging to the genus Aspergillus, Endomyces or Rhizopus. By employing the glucoamylase in an amount within the specified range and at a temperature in the specified range, saccharification proceeds at such a rate that within a period of three hours the D.E. of the saccharified mass is at least 90. Thus, the present invention provides an improved process for the conversion of starch to syrups having a D.E. value of at least 90, and preferably 95, which is achieved by treating liquefied starch with glucoamylase for a period of not more than three hours.

The saccharified starch slurry or syrup can, if desired, be refined by conventional refinery materials. These include treatment with carbon, ion exchange resins, filtration, centrifugation and the like. For many end uses, such as in the fermentation or brewery arts, the saccharified syrup having a D.E. value of at least 90 can be used without any additional treatment or refining.

The following examples illustrate the invention and the advantages thereof.

EXAMPLE 1

Liquefaction

Whole ground corn was slurried in water in an amount of 3.82 pounds of corn per gallon of water (38.9% dry solids basis) at a pH of 6.7. The slurry was passed through a jet cooker wherein it was exposed to a temperature of 325° F. (162.8° C.) at 80 psig pressure for three minutes. The cooked slurry was then held for one hour at a temperature of 205° F. (96° C.) together with 0.3% (enzyme on starch dry solids basis) of a bacterial alpha-amylase available from the Novo Enzyme Corporation, Mamaroneck, N.Y. under the tradename Termamyl. At the end of the liquefaction period, the D.E. of the liquefied slurry was approximately 20.

Saccharification

The liquefied starch was then converted to a dextrose-containing syrup. To this end, the pH of the slurry was then adjusted to 4.5 and held at a temperature of 160° F. (71° C.) together with glucoamylase (Miles Diazyme L-100) which was employed at a level of 1 amyloglucosidase unit per gram of starch. (Activity of enzyme was 100 AGU/gram. The quantity added was 1% as is on starch dry basis.)

At the end of two hours of conversion with the glucoamylase, the D.E. of the resulting syrup was 91.4. The syrup was utilized in a fermentation after which it was tested and found to contain no residual fermentation sugars and thus the hydrolyzate syrup represented a suitable substrate for fermentation use.

EXAMPLE 2

Liquefaction

An aqueous slurry of unmodified corn starch containing 38.7% by weight starch (dry solids basis) was passed through a jet cooker wherein it was exposed to a temperature of 325° F. (162.8° C.) at 80 psig pressure for three minutes. The bacterial alpha-amylase, Termamyl, was added in increments to provide 0.2% by weight enzyme on starch (dry solids). The substrate was held at 205° F. (96° C.) for approximately one hour. The D.E. of the liquefied slurry was estimated to be 15–20, but was not determined by assay.

Saccharification

The liquefied starch at a solids concentration of 40% by weight (dry solids) was adjusted to pH 4.5 and to a temperature of 165° F. (73.9° C.). Glucoamylase (Miles Diazyme L-100) was employed at a level of 0.8 amyloglucosidase unit per gram of starch (0.8% dry starch basis).

At the end of three hours of conversion with the glucoamylase, the D.E. of the resulting syrup was 97.2. The syrup was analyzed by high pressure liquid chromatography as follows:

| | |
|---|---|
| $DP_1$ | 86.9 |
| $DP_2$ | 3.4 |
| $DP_3$ | — |
| $DP_{Higher\ than\ 3}$ | 9.7 |

EXAMPLE 3

An aqueous slurry of a commercial corn starch hydrolyzate, MALTRIN M-200*, having a D.E. of 22.6 at a concentration of 30% by weight (dry solids) was prepared. The pH of the substrate was adjusted to 4.5 and then treated with varying amounts of glucoamylase at a temperature of 165° F. (73.9° C.) for various periods as shown below. Samples were removed and analyzed at various periods as shown below:

*MALTRIN M-200 is a commercially available (Grain Processing Corporation, Muscatine, Iowa) corn starch hydrolyzate having a D.E. value of approximately 20 produced in accordance with U.S. Pat. No. 3,663,369.

| | Sample | | | |
|---|---|---|---|---|
| | I | II | III | IV |
| | \multicolumn{4}{c}{Enzyme Level (wt./wt.)} | | | |
| | 0.2% D.E. | 0.4% D.E. | 0.8% D.E. | 1.6% D.E. |
| 1 hour | 62.9 | 78.0 | 84.9 | 89.9 |
| 2 hours | 69.9 | 82.6 | 90.0 | 99.4 |
| 3 hours | 78.5 | 88.9 | 96.0 | 100 |
| 4 hours | 81.1 | 91.3 | 97.6 | 100 |

EXAMPLE 4

An aqueous slurry of MALTRIN M-200 having a D.E. of 24 at a concentration of 40% by weight (dry solids) was prepared. The pH of the slurry was adjusted to 4.5 and then treated with a glucoamylase at a temperature of 170° F. (76.7° C.) for various periods as shown below:

| | Sample | | | |
|---|---|---|---|---|
| | I | II | III | IV |
| | \multicolumn{4}{c}{Enzyme Level (wt./wt.)} | | | |
| | 0.2% D.E. | 0.4% D.E. | 0.8% D.E. | 1.6% D.E. |
| 1 hour | 57.0 | 71.4 | 91.2 | 96.0 |
| 2 hours | 68.2 | 78.7 | 96.5 | 97.4 |
| 3 hours | 73.6 | 80.2 | 99.5 | 100 |
| 4 hours | 78.5 | 86.0 | 100 | 100 |

EXAMPLE 5

An aqueous slurry of MALTRIN M-200 having a D.E. of 23 at a concentration of 45% by weight dry solids was prepared. The pH of the slurry was adjusted to 4.5 and then treated with a glucoamylase at a temperature of 175° F. (79.4° C.) for various periods as shown below:

| | Sample | | | |
|---|---|---|---|---|
| | I | II | III | IV |
| | \multicolumn{4}{c}{Enzyme Level (wt./wt.)} | | | |
| | 0.2% D.E. | 0.4% D.E. | 0.8% D.E. | 1.6% D.E. |
| 1 hour | 49.5 | 64.8 | 84.1 | 93.8 |
| 2 hours | 58.6 | 69.5 | 91.5 | 95.8 |
| 3 hours | 63.4 | 73.1 | 93.9 | 95.0 |
| 4 hours | 67.2 | 74.1 | 93.9 | 93.1 |

EXAMPLE 6

An aqueous slurry of MALTRIN M-200 having a D.E. of 23 at a concentration of 50% by weight (dry solids) was prepared. The pH of the slurry was adjusted to 4.5 and then treated with a glucoamylase at a temperature of 175° F. (79.4° C.) for various periods as shown below:

| | Sample | | | |
|---|---|---|---|---|
| | I | II | III | IV |
| | \multicolumn{4}{c}{Enzyme Level (wt./wt.)} | | | |
| | 0.2% D.E. | 0.4% D.E. | 0.8% D.E. | 1.6% D.E. |
| 1 hour | 45.3 | 60.0 | 87.7 | 93.6 |
| 2 hours | 51.8 | 64.1 | 95.0 | 96.7 |

-continued

| | Sample | | | |
|---|---|---|---|---|
| | I | II | III | IV |
| | Enzyme Level (wt./wt.) | | | |
| | 0.2% D.E. | 0.4% D.E. | 0.8% D.E. | 1.6% D.E. |
| 3 hours | 51.8 | 64.5 | 99.7 | 99.8 |
| 4 hours | 59.8 | 74.8 | 100 | 97.9 |

EXAMPLE 7

Liquefaction

An aqueous slurry of unmodified corn starch 30% by weight starch (dry solids) was passed through a jet cooker wherein it was exposed to a temperature of 315°–320° F. (157.22°–160° C.) at 80 psig pressure for five minutes. The cooked starch was adjusted to a temperature of 205° F. (96° C.). Bacterial alpha-amylase, Termamyl and BAN 120 L (a liquid bacterial alpha-amylase available from the Novo Enzyme Corporation, Mamaroneck, N.Y.), were added in increments to provide 0.15% by weight of each enzyme of starch (dry solids). The D.E. of the liquefied slurry was estimated to be in the range 20–25, but was not determined by assay.

Saccharification

The pH of the liquefied substrate was then adjusted to 4.3–4.5 and held at a temperature of 165° F. (73.9° C.) together with AMG 150 (a liquid exo-amylase produced from *Aspergillus niger* and available from Novo Enzyme Corporation, Mamaroneck, N.Y.) which was employed at a level of 0.8% by weight of starch.

At the end of three hours of conversion with the glucoamylase, the D.E. determined by titration of the resulting syrup was 95.8. The syrup was analyzed by high pressure liquid chromatography as follows:

| $DP_1$ | 91.3 |
|---|---|
| $DP_2$ | 2.4 |
| $DP_3$ | 0.2 |
| $DP_4$ | 0.3 |
| $DP_{Higher\ than\ 4}$ | 5.8 |

EXAMPLE 8

Liquefaction

An aqueous slurry of unmodified corn starch at a concentration of 30% starch (dry solids) was passed through a jet cooker wherein it was exposed to a temperature of 320° F. (160° C.) at 80 psig pressure for five minutes. The cooked starch was adjusted to a temperature of 205° F. (96.1° C.). The bacterial alpha-amylases Termamyl and BAN 120 L were added in increments to provide 0.05% by weight of each enzyme based on starch (dry solids). At the end of the liquefaction period, 30 minutes, the D.E. of the liquefied substrate was estimated to be 10.

Saccharification

The pH of the substrate was then adjusted to 4.5 and held at a temperature of 155° F. (68.33° C.) together with glucoamylase for periods as shown. Analysis was as follows:

| | Dextrose Equivalent | | |
|---|---|---|---|
| | Sample | | |
| | I | II | III |
| | Enzyme Level (wt./wt.) | | |
| | 0.4% | 0.6% | 0.8% |
| 2 hours | 93.6 | 98.8 | 100 |
| 3 hours | 98.9 | 100 | 100 |
| 4 hours | 95.0 | 100 | 100 |
| Profile (3 hours) | | | |
| $DP_1$ | 84.7 | 91.4 | 91.5 |
| $DP_2$ | 2.6 | 2.3 | 1.3 |
| $DP_3$ | 0.4 | 0.2 | 0.1 |
| $DP_{Higher\ than\ 3}$ | 12.4 | 6.0 | 7.0 |

EXAMPLE 9

Liquefaction

An aqueous slurry of unmodified corn starch at a concentration of 30% starch (dry solids) was passed through a jet cooker wherein it was exposed to a temperature of 320° F. (160° C.) at 72 psig pressure for five minutes. The cooked starch was then adjusted to 205° F. (96.1° C.). The bacterial alpha-amylases Thermamyl and BAN 120 L were added in increments to provide 0.05% by weight of each enzyme based on starch (dry solids). At the end of the liquefaction period, 30 minutes, the D.E. of the liquefied slurry was estimated to be 12–15.

Saccharification

The pH of the slurry was then adjusted to 4.5 and held at a temperature of 165° F. (73.9° C.) together with a glucoamylase for periods as shown. Analysis produced the following results:

| | Dextrose Equivalent | | |
|---|---|---|---|
| | Sample | | |
| | I | II | III |
| | Enzyme Level (wt./wt.) | | |
| | 0.4% | 0.6% | 0.8% |
| 2 hours | 86.8 | 92.8 | 97.7 |
| 3 hours | 90.7 | 95.0 | 98.7 |
| 4 hours | 93.0 | 98.4 | 100 |
| Profile (3 hours) | | | |
| $DP_1$ | 72.0 | 83.6 | 88.6 |
| $DP_2$ | 5.4 | 3.2 | 2.4 |
| $DP_3$ | 1.3 | 0.3 | 0.2 |
| $DP_{Higher\ than\ 3}$ | 21.3 | 12.9 | 8.8 |

EXAMPLE 10

A suspension of hydrolyzed cereal solids at an approximate D.E. of 20 was prepared at a concentration of 30% (dry solids). Calcium chloride dihydrate was added at an equivalent of 0.15% by weight of starch (dry solids). The pH was adjusted to 4.5 and the temperature to 160° F. (71.1° C.). To this substrate was added a dilute solution of *Aspergillus awamori* with an activity level of 1.288 amyloglucosidase units per gram of substrate.

Conversion was monitored by determining dextrose equivalent at one hour intervals with the results being as follows:

| Time | D.E. |
|---|---|
| 1 hour | 90.6 |

-continued

| Time | D.E. |
| --- | --- |
| 2 hours | 95.8 |
| 3 hours | 96.8 |
| 4 hours | 96.1 |

FIG. 1 is a plot of data showing the average sum of $DP_1$ and $DP_2$ saccharides for reaction periods of 2, 3 and 4 hours obtained using different amounts of glucoamylase based on weight of starch substrate at different reaction temperatures. The plotted data indicates that the sum of $DP_1$ and $DP_2$ saccharides was less at a reaction temperature of 80° compared to quantities produced at lower reaction temperatures.

Figure 2:
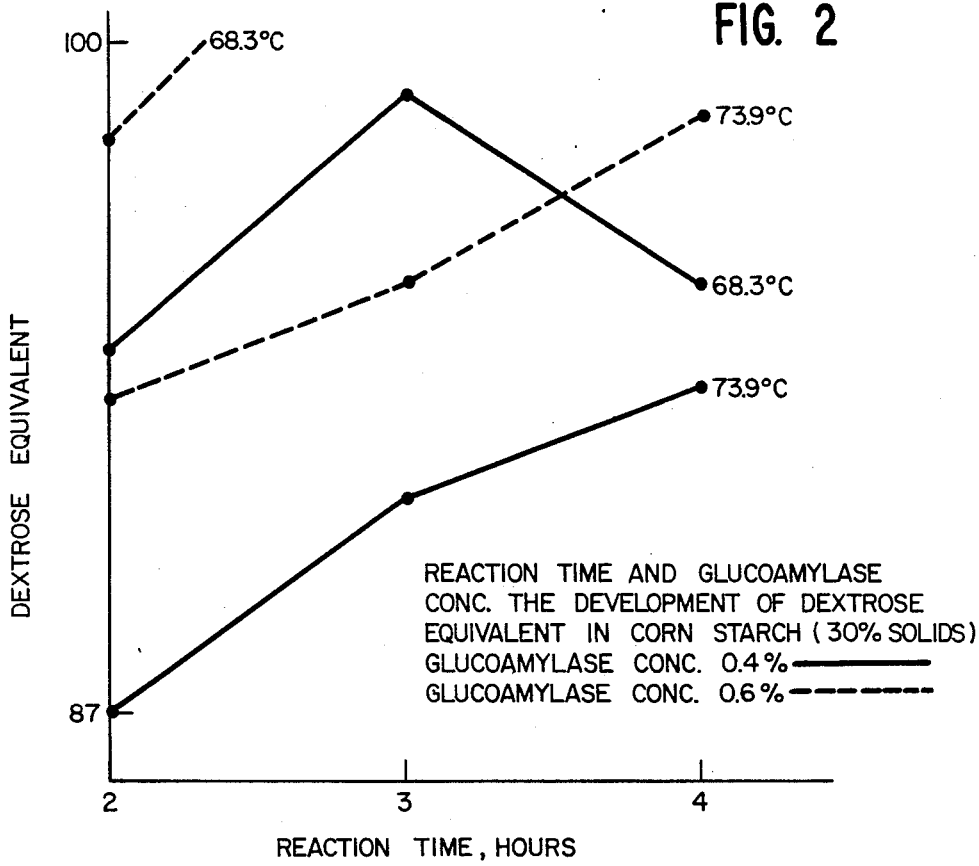

FIG. 2 is a plot of data showing dextrose equivalent values obtained with differing reaction times and reaction temperatures.

Those modifications and equivalents which fall within the spirit of the invention are to be considered a part thereof.

What is claimed is:

1. A process for producing a dextrose-containing syrup which comprises liquefying a substrate containing at least about 30% by weight of starch (dry basis), treating at a temperature of from 150° F. to 175° F. the liquefied substrate with a fungal glucoamylase in sufficient amount to provide from 0.5 to 2.0 amyloglucosidase unit per gram of starch and to produce a syrup having a dextrose equivalent value of at least 90 in a period of not more than 3 hours.

2. A process in accordance with claim 1 wherein the starch substrate is cooked at a temperature in the range of about 250° to 325° F. prior to liquefying.

3. A process in accordance with claim 1 wherein the syrup having a dextrose equivalent value of at least 90 after treatment with glucoamylase is further refined.

4. A process in accordance with claim 1 wherein the fungal glucoamylase is one belonging to the genus Aspergillis, Endomyces or Rhizopus.

* * * * *